United States Patent
Wunderlich et al.

(10) Patent No.: US 6,176,237 B1
(45) Date of Patent: Jan. 23, 2001

(54) INHALATION THERAPY UNIT WITH A VALVE FOR LIMITING THE INSPIRATION FLOW

(75) Inventors: Eric Wunderlich, Gilching; Robert Waldner, Peiting; Martin Knoch, Berg, all of (DE)

(73) Assignee: PARI GmbH Spezialisten fur effektive Inhalation, Starnberg (DE)

( * ) Notice: Under 35 U.S.C. 154(b), the term of this patent shall be extended for 0 days.

(21) Appl. No.: 09/129,211

(22) Filed: Aug. 4, 1998

(30) Foreign Application Priority Data

Aug. 6, 1997 (DE) ............................... 197 34 022

(51) Int. Cl.⁷ .................................................. A61M 15/00
(52) U.S. Cl. ................................. 128/203.12; 128/205.24
(58) Field of Search ..................... 128/200.21, 203.12, 128/205.24, 200.14, 207.12, 207.16

(56) References Cited

U.S. PATENT DOCUMENTS

| 4,007,758 | 2/1977 | Gray et al. . |
| 4,210,174 | 7/1980 | Eross . |
| 4,838,262 | * 6/1989 | Katz ................................ 128/205.24 |
| 5,584,285 | * 12/1996 | Salter et al. ..................... 128/202.27 |
| 5,584,288 | * 12/1996 | Baldwin .......................... 128/205.24 |
| 5,704,347 | 1/1998 | Schlobohm . |
| 5,738,087 | * 4/1998 | King ................................ 128/205.24 |
| 5,937,850 | * 8/1999 | Kawashima et al. ........... 128/205.24 |
| 5,937,857 | * 8/1999 | Caterini et al. ................. 128/205.11 |

FOREIGN PATENT DOCUMENTS

| 76 03 903 U | 7/1976 | (DE) . |
| 26 48 927 C3 | 10/1976 | (DE) . |
| 36 15 664 C2 | 5/1986 | (DE) . |
| 37 01 375 A1 | 1/1987 | (DE) . |
| 43 27 531 C2 | 8/1993 | (DE) . |
| 195 32 042 C1 | 8/1995 | (DE) . |
| 0 281 650 | 9/1988 | (EP) . |

* cited by examiner

Primary Examiner—Aaron J. Lewis
Assistant Examiner—Teena Mitchell
(74) Attorney, Agent, or Firm—Merchant & Gould P.C.

(57) ABSTRACT

A limiting valve (4) is provided in an inhalation therapy unit with a valve member (13) which closes an air through opening (12) in the idle state and corresponding to the pressure difference occurring over the valve opens same substantially proportionally up to a threshold value. If the threshold value is exceeded, the valve member (13) abuts against a limiting member (16) which limits the movement of the valve member (13) and the air passage orifices (17) of which are partially closed by the valve member (13) so that air can only flow through the air passage auxiliary orifices remaining free. In this manner the patient using the inhalation therapy unit is urged to breath in the range below the threshold value, as his respiration above the threshold value is opposed by a considerably higher resistance.

8 Claims, 3 Drawing Sheets

INHALATION THERAPY UNIT WITH A VALVE FOR LIMITING THE INSPIRATION FLOW

BACKGROUND OF THE INVENTION

The present invention relates to inhalation therapy units and especially to a valve for limiting the inspiration flow.

An aerosol atomizer is known from the EP-B-0 281 650, which consists of a substantially cylindrical basic body in which an atomizer nozzle is disposed for the generation of an aerosol and into which an air intake flue projects for the supply of ambient air. The outer opening of the air intake flue is closed by an inlet valve which is constructed as one-way valve. It permits the inflow of ambient air into the nebuliser housing when the patient inspires through a mouthpiece of the aerosol atomizer, but prevents the escape of the aerosol from the atomizer interior during the breathing intervals and for the event that the patent exhales into the aerosol atomizer. The known inhalation therapy unit is therefore constructed in such a manner that the patient can inspire an arbitrary volume of respiratory air, limited merely by the flow resistance defined by the shape of the atomizer.

However, the aim of an inhalation therapy is always the effective, low side-effect application of the medicine administered in aerosol form into the diseased lung regions. In this respect, an aerosol is generated in an inhalation therapy unit with a suitable droplet spectrum and in a suitable amount. This aerosol should be inhaled by the patient according to a defined breathing pattern, so that the aerosol droplets reach the desired deposition location in the lungs. Until now, it was necessary to train the patient with a view to this breathing pattern and an optimization of the breathing parameters, which in many cases led to considerable difficulties.

In these efforts, there are two contradictory requirements. On the one hand, namely, the inspiring of the aerosol should be as easy as possible for the patient, and on the other hand, a maximization of the effect of the inhalation therapy only occurs when an aerosol is inspired in such a manner that a deposition takes place at the desired location of the lungs. This procedure is influenced by the droplet size, the amount of aerosol, the amount of intake air, the inspiration flow and other parameters. With respect to the inspiration flow, until now it was only endeavoured to achieve a limitation in the inspiration path of the inhalation therapy unit by cross-section reductions (stenoses). Due to the increased flow resistance in the flow region to be realized, however, this frequently results in the encumbrance of the already weakened respiratory capacity of the patient.

An inspiration flow of up to a maximum of 30 l/min is aerosol-physically desirable in order to minimize the inertial separation, the so-called impaction, of the aerosol droplets in the upper respiratory paths and to increase the deposition probability in the lungs in the intended deposition location.

The expiratory process is of lesser significance. However, also during expiration the expiration flow should be within a certain range.

With this background, the object of the invention is to construct an inhalation therapy unit in such a manner that the maintenance of the aerosol-physically desirable ranges is simplified for the patient during respiration, without an additional encumbrance occurring for the patient upon respiration in these ranges.

SUMMARY OF THE INVENTION

This object is solved by an inhalation therapy unit comprising a nebulisation chamber in which an aerosol is generated with the aid of an atomizer nozzle, a connecting piece via which the aerosol is led out of the nebulisation chamber, an air inlet means through which the ambient air enters into the nebulisation chamber, and an inlet valve which includes at least one inlet opening and a valve member closing the inlet opening and which is arranged in the air inlet means in such a manner that an underpressure in the nebulisation chamber moves the valve member to release the inlet opening, a limiting member being provided in the inlet valve, which limits the movement of the valve member in such a manner that the release of the inlet opening is substantially proportional to the underpressure only up to a threshold value of the underpressure in the nebulisation chamber.

In a special configuration of this solution, the limiting member comprises at least one passage orifice, which is partially closed by the valve member when the valve member is moved until it is against the limiting member by an underpressure exceeding the threshold value in the nebulisation chamber.

The problem on which the invention is based is further solved in general by an inhalation therapy unit with a valve, which comprises at least one through opening and a valve member which is moved on account of a pressure difference present across the valve so that it closes the through opening when the pressure difference across the valve is present in the one direction and releases the through opening when the pressure difference across the valve is present in the other direction, and a limiting member is provided that limits the movement of the valve member in such a manner that the release of the through opening is substantially proportional to the pressure difference only up to a threshold value of the pressure difference.

In a special configuration of this solution, the limiting member comprises at least one passage orifice which is partially closed by the valve member when the valve member is moved by a pressure difference exceeding the threshold value over the valve until it is against the limiting member.

In both solutions it is advantageous for the valve member to be a circular valve platelet, wherein the passage orifice of the limiting member projects at least section-wise beyond the contour of the valve platelet in the region of the outer edge of the valve platelet.

It is furthermore advantageous if the contour of the air passage orifice (17) of the limiting member (16) interacting with the valve platelet is of undulatory or zig-zag shape.

The valve member is preferably formed of silicone or another elastic material.

For use in aerosol therapy, the invention signifies that the inhalation therapy unit is equipped with a limiting valve which is adaptable to the lung-physiological parameters of the patient and controls the inspiration flow of the patient as a passive controller of the threshold value. By means of a strongly progressive pressure/flow characteristic above a certain flow threshold value, it is achieved that the patient recognizes by the flow resistance felt upon inspiration that he lies outside the aerosol-physically desirable range. He can then adapt his breathing behaviour accordingly. Within the aerosol-physically desirable range, the patient feels practically no increase of the flow resistance in comparison to an inhalation therapy unit without the passive limiting valve according to the invention.

The limiting valve described in the following in more detail on the basis of an embodiment has furthermore the advantage that it is realized in an extremely simple manner and the desired aims thus can be achieved in an economical manner.

BRIEF DESCRIPTION OF THE DRAWINGS

The invention is explained in more detail in the following on the basis of an embodiment with reference to the figures, in which there are shown.

DETAILED DESCRIPTION

Figure 1:
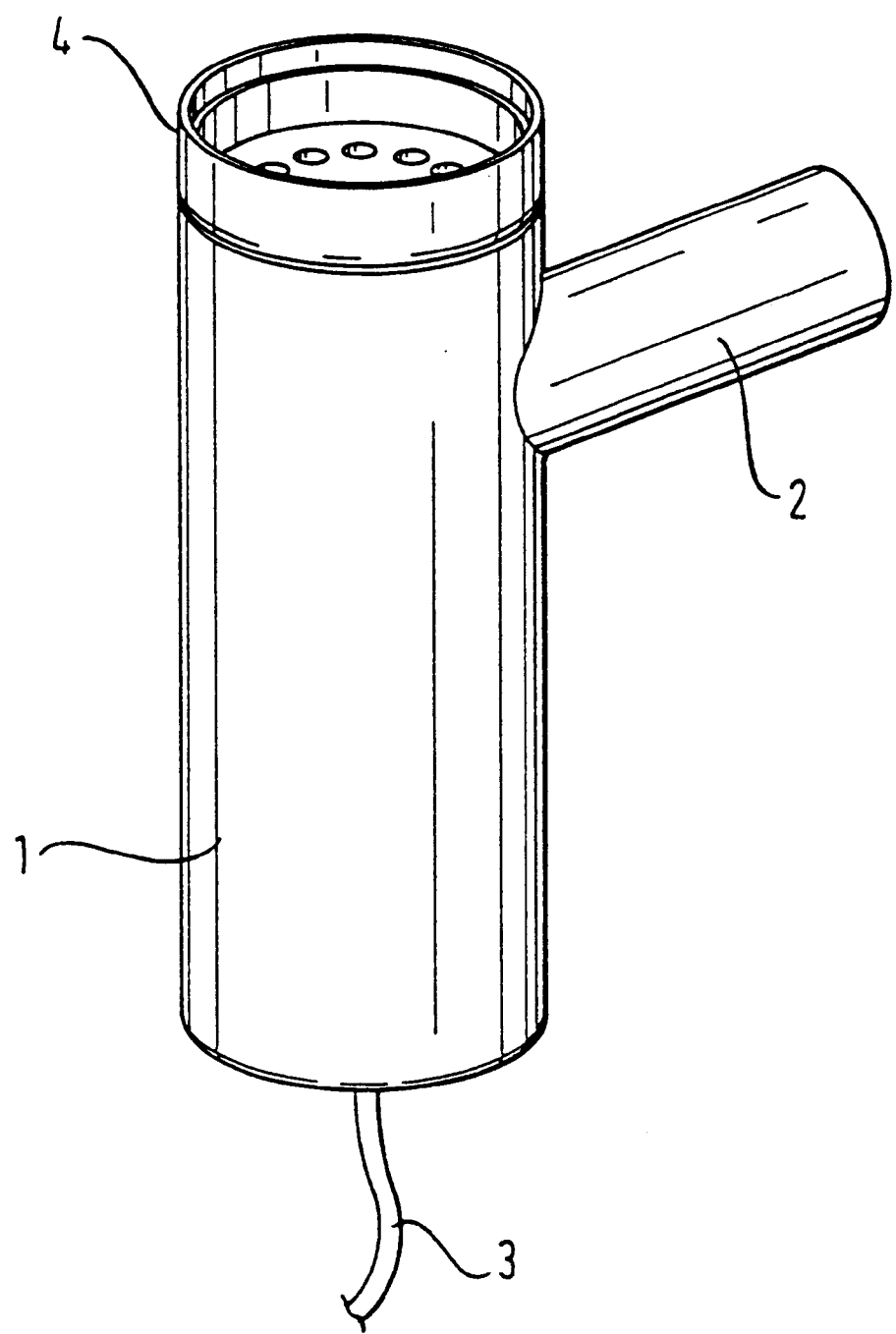
FIG. 1 an inhalation therapy unit with a limiting valve according to the invention.

In FIG. 1 an inhalation therapy unit is represented, which includes a cylindrical basic body 1 and a connecting piece 2 formed thereon. In the interior of the cylindrical basic body 1, i.e. in the nebulisation chamber, an atomizer nozzle (not shown, see e.g. EP-B-0 281 650) is arranged, which generates an aerosol from a medicine stored in the inhalation therapy unit. For this purpose, compressed air is supplied to the atomizer nozzle via a pressure medium supply line 3. A mouthpiece is generally arranged on the connecting piece 2 via which the patient can inspire the aerosol generated in the nebulisation chamber. From the upper end of the cylindrical basic body 1 in FIG. 1 a cylindrical air intake flue (not shown, see for example EP-B-0 281 650) projects into the nebulisation chamber. Through this air intake flue, ambient air can further flow into the interior of the inhalation therapy unit when the patient inspires the aerosol via the mouthpiece mounted on the connecting piece 2. The outwardly facing opening of the air intake flue is closed by a passive limiting valve 4, which is constructed as one-way valve and the assembly of which is described in more detail in the following with reference to FIG. 2.

Figure 2A:
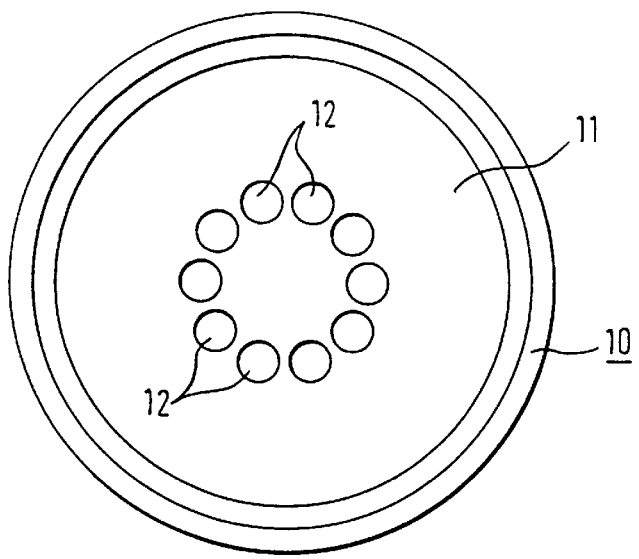
FIGS. 2A to 2C the limiting valve of FIG. 1 in different views.
Figure 2B:
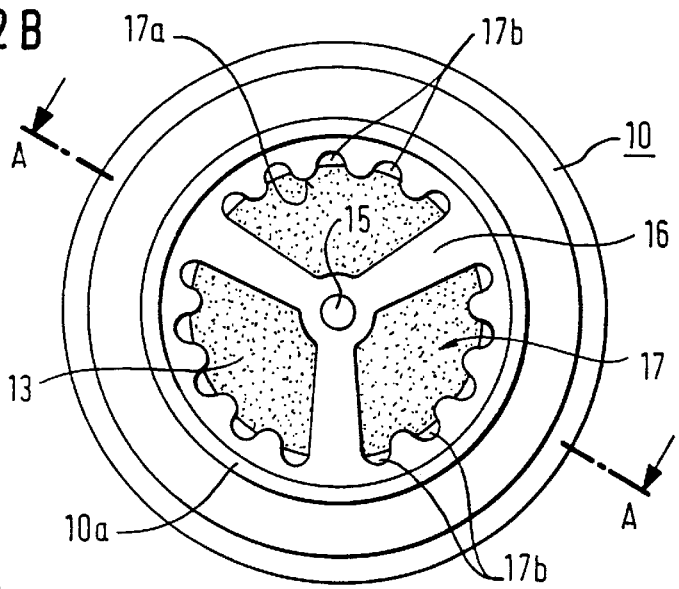
Figure 2C:
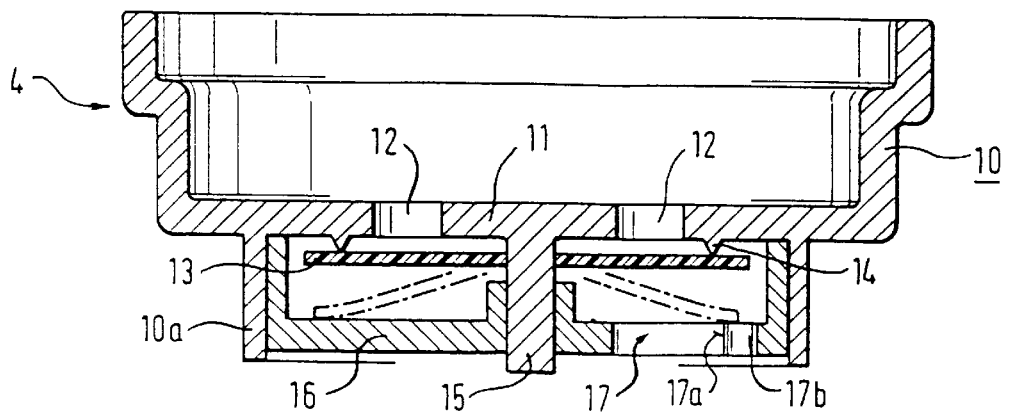

FIG. 2A shows the passive limiting valve 4 from the outwardly facing side, i.e. from the side to be seen also in FIG. 1. FIG. 2B shows the passive limiting valve 4 on the side facing the air intake flue, which is not visible in FIG. 1. FIG. 2C shows a cross-section through the passive limiting valve along the line A—A in FIG. 2B.

In FIGS. 2A to 2C it can be seen that the passive limiting valve 4 of the embodiment of the invention here described includes a cylindrical basic body 10 having a surface formed in a plurality of stages and a closure wall 11 perpendicular to the cylinder axis. In the closure wall 11, a plurality of air inlet openings 12 are provided, which can also be defined as through openings and through which ambient air can flow into the interior of the inhalation therapy unit. In the cylinder section 10a with the smallest outer diameter, a valve member 13 is provided which has the shape of a circular valve platelet with a centric securement opening. The valve platelet 13 is made of an elastic material, for example silicone, with a sufficient stiffness of its own which guarantees that the valve platelet 13, in the non-deflected idle position, closes the air inlet openings 12 of the limiting valve 4. As can be recognized in FIG. 2C, a circular sealing lip 14 can be provided as support on the side of the closure wall 11 facing the valve platelet. For securement, the valve platelet 13 is placed on a pin 15 extending along the cylinder axis on the side of the limiting valve 4 facing the interior of the inhalation therapy unit.

By this assembly, the following function is realized. When the patient breathes through the inhalation therapy unit, the valve platelet is deflected and permits the flowing in of intake air through the air inlet openings 12 of the limiting valve. The resultant opening cross-section is extensively proportional to the underpressure which has built up in the nebuliser chamber. In the breathing intervals, or when the patient expires into the inhalation therapy unit, the valve member 13 closes the openings 12.

According to the invention, on the side of the valve platelet 13 lying opposite the closure wall 11, a limiting member 16 is arranged which limits the deflection of the valve platelet 13. The limiting element 16 has the shape of a circular disc with a centrically arranged securement opening. The outer diameter of the limiting member 16 substantially corresponds with the inside diameter of the cylinder section 10a. The limiting member 16 is also placed on the pin 15 extending along the cylinder axis, so that the valve platelet 13 and the limiting member 16 are aligned with each other. The limiting member 16 has air passage orifices 17, which are sufficiently large so as not to offer any great resistance to the flowing through of the suctioned air when the valve platelet 13 is only deflected so far that it does not abut against the limiting member 16. The ambient air then flows through the air inlet openings 12 and around the valve platelet 13 in order subsequently to enter into the interior of the inhalation therapy unit via the air passage orifices 17. Via the self restoring force of the valve platelet 13, a flow path is created having an opening cross-section which is proportional to the underpressure in the interior of the inhalation therapy unit, i.e the pressure difference across the valve, as long as the patient breathes within the aerosol-physically desirable pressure/flow range.

Figure 3:
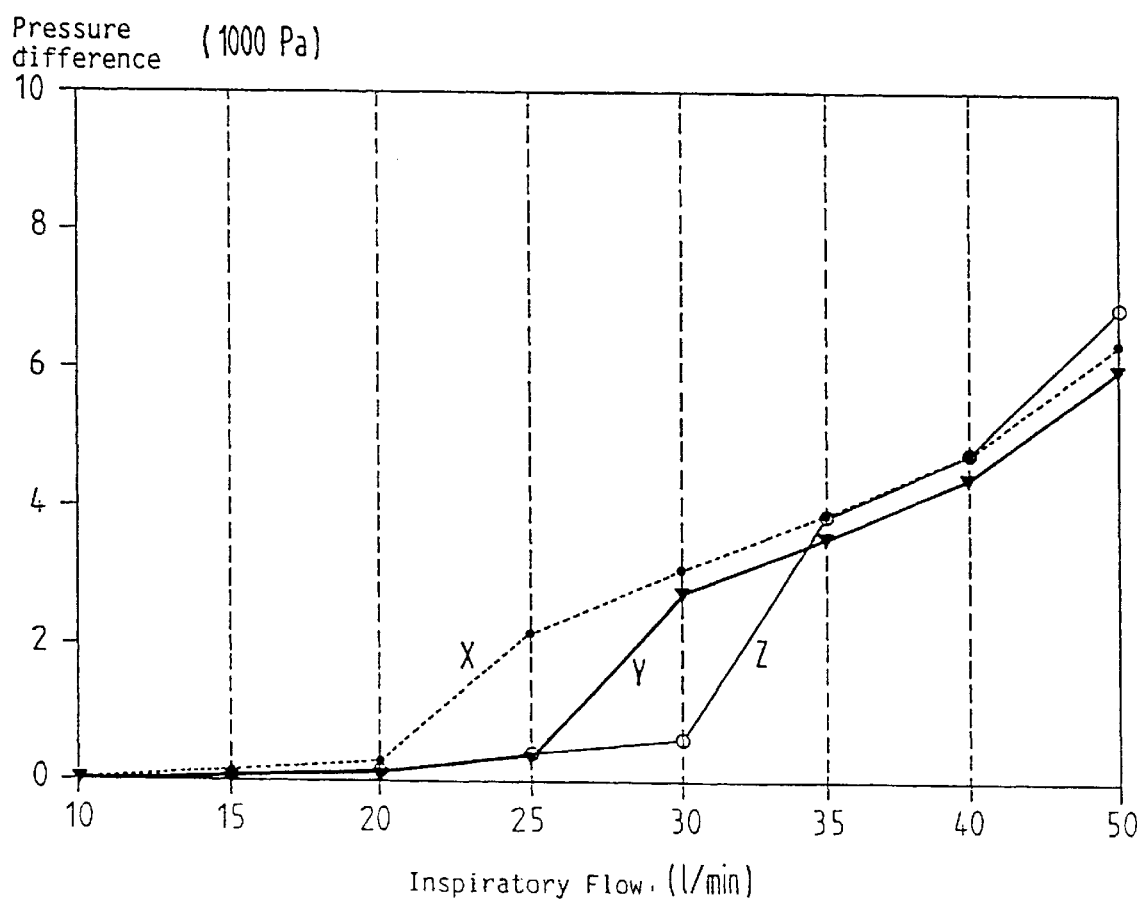
FIG. 3 a diagram of the pressure/flow ratio in an inhalation therapy unit according to the invention.

If the underpressure exceeds a certain limit, the valve platelet 13 abuts against the facing surface of the limiting member 16, whereby the air passage orifices 17 of the limiting member are almost completely closed. On account of the shape of the air passage orifices 17, however, the orifices remaining open for the passage of air have a strongly reduced cross-section. The remaining orifices are defined in the following as air passage auxiliary orifices; they can be provided separately from the air passage orifices 17, or realized as part of these orifices. The cross-section of these orifices does not change any more if the underpressure is further increased, i.e. if the patient tries to inspire more strongly. This leads to an exponentially increasing flow-through resistance upon a further increase of the underpressure, as can be taken from the diagram in FIG. 3 (see curves x, y and z). This finally leads to a reduction of the inspiration flow in the desired target value range. This target value range is dependent on the deflection of the valve platelet and on the cross-section of the auxiliary openings and can therefore be adjusted in broad limits.

The air passage orifices 17 of the limiting member 16 are advantageously constructed so that they have as large an area as possible and are aligned with the valve platelet 13. The contour 17a of the air passage orifices 17 extending along the outer edge of the valve platelet is designed in the shown embodiment in such a manner that even upon abutment of the valve platelet 13 a part of the air passage orifices 17 remain open as auxiliary orifices 17b through which air can further flow. These auxiliary orifices are very much smaller than the air passage orifices. The previously mentioned contour of the air passage orifices 17 is for example of undulatory or zig-zag shape.

FIG. 2B reveals an undulatory shape of the contour 17a of the air passage orifices 17 in the region corresponding to the outer edge of the valve platelet. If the valve platelet 13 abuts against the limiting member 16, only the radially outwardly projecting sections of the air passage orifices 17 remain open as auxiliary orifices 17b whereas the far greater portion of the air passage orifices is closed by the valve platelet 13.

Accordingly, the corresponding contour 17a of the air passage orifice 17 of the limiting member 16 interacts with the outer edge of the valve platelet 13, so that also when the valve platelet 13 abuts, orifices remain through which the air can flow. These orifices are preferably parts of the air passage orifices 17 which, when the valve platelet does not abut against the limiting element as a whole are available for the flow-through of the air.

However, when the valve platelet abuts, these sections represent auxiliary orifices through which air can further flow, but on account of the reduced cross-section, with an increased flow resistance. The interaction of the outer edge of the valve platelet with the corresponding contour of the air passage orifice represents a special characteristic of the invention. With this construction, a valve is created which provides, with increasing pressure difference, firstly proportional air passage orifices with maximum cross-section, and upon reaching a threshold value of the pressure difference, only air passage auxiliary orifices with clearly reduced and constant cross-sectional area for the air flow.

We claim:

1. An inhalation therapy unit, comprising:
   a nebulisation chamber in which an aerosol is generated with an atomizing nozzle;
   a connecting piece through which aerosol is lead out of the nebulisation chamber;
   an air inlet through which ambient air enters the nebulisation chamber;
   an inlet valve comprising an inlet opening and a valve member closing the inlet opening, arranged in the air inlet so that an underpressure in the nebulisation chamber moves the valve member to open the inlet opening; and
   a limiting member provided in the inlet valve that limits the movement of the valve member so that the opening of the inlet opening is substantially proportional to the under pressure in the nebulisation chamber only up to a threshold value of the underpressure.

2. An inhalation therapy unit according to claim 1, wherein the limiting member comprises at least one air passage opening, said air passage opening being partially closed by the valve member when the valve member is moved to contact the limiting member by an underpressure in the nebulisation chamber exceeding the threshold value.

3. An inhalation therapy unit according to claim 2, wherein the valve member is a circular valve platelet and the air passage opening projects at least partially beyond an outer edge of the valve platelet when the valve platelet contacts the limiting member.

4. An inhalation therapy unit according to claim 3, wherein the contour of the air passage opening has an undulatory or zig-zag shape.

5. An inhalation therapy unit according to claim 1, wherein the valve member is formed of an elastic material.

6. An inhalation therapy unit, comprising an air passage;
   a valve comprising a valve member which moves in response to a pressure difference across the valve so as to close the air passage when the pressure difference across the valve is present in one direction and opens the air passage when the pressure difference across the valve is present in a second direction; and
   a limiting member that limits the movement of the valve member so that the opening of the air passage is substantially proportional to the pressure difference only up to a threshold value, the limiting member comprising an air passage opening that is partially closed by the valve member when the valve member is moved against the limiting member by a pressure difference exceeding the threshold value, the valve member comprising a circular valve platelet and the air passage opening of the limiting member projecting at least partially beyond an outer edge of the valve platelet when the valve platelet is in contact with the limiting member.

7. An inhalation therapy unit according to claim 6, wherein the valve member is formed of an elastic material.

8. An inhalation therapy unit according to claim 6, wherein the contour of the air passage opening has an undulatory or zig-zag shape.

* * * * *